(12) United States Patent
Pappas et al.

(10) Patent No.: US 10,238,892 B2
(45) Date of Patent: Mar. 26, 2019

(54) SYSTEM AND METHOD FOR PATIENT-SPECIFIC RADIOTHERAPY TREATMENT VERIFICATION AND QUALITY ASSURANCE SYSTEM

(71) Applicants: Evangelos T. Pappas, Athens (GR); Thomas G. Maris, Heraklion (GR)

(72) Inventors: Evangelos T. Pappas, Athens (GR); Thomas G. Maris, Heraklion (GR)

( * ) Notice: Subject to any disclaimer, the term of this patent is extended or adjusted under 35 U.S.C. 154(b) by 123 days.

(21) Appl. No.: 15/067,333

(22) Filed: Mar. 11, 2016

(65) Prior Publication Data
US 2016/0256711 A1    Sep. 8, 2016

Related U.S. Application Data

(63) Continuation of application No. PCT/IB2014/002624, filed on Sep. 9, 2014.

(60) Provisional application No. 61/876,269, filed on Sep. 11, 2013.

(51) Int. Cl.
*A61N 5/10* (2006.01)
*A61B 5/055* (2006.01)

(52) U.S. Cl.
CPC ............ *A61N 5/1039* (2013.01); *A61B 5/055* (2013.01); *A61N 5/1075* (2013.01); *A61N 5/1071* (2013.01); *A61N 2005/1076* (2013.01)

(58) Field of Classification Search
CPC .. A61N 5/1071; A61N 5/1031; A61N 5/1075; A61N 2005/1076; A61B 6/583; A61B 6/5229
See application file for complete search history.

(56) References Cited

U.S. PATENT DOCUMENTS

| 7,639,854 B2 | 12/2009 | Schnarr et al. |
| 2006/0241445 A1 | 10/2006 | Altmann et al. |

(Continued)

FOREIGN PATENT DOCUMENTS

| CN | 1669599 A | 9/2005 |
| CN | 101011617 A | 8/2007 |

(Continued)

OTHER PUBLICATIONS

Radaideh et al., Development and evaluation of a Perspex anthropomorphic head and neck phantom for three dimensional conformal radiation therapy (3D-CRT), Journal of Radiotherapy in Practice (2013) 12, 272-280.

(Continued)

*Primary Examiner* — Kenneth J Malkowski
(74) *Attorney, Agent, or Firm* — Robert R. Riddle; Matthew S. Gibson; Reed Smith LLP

(57) ABSTRACT

A radiotherapy treatment verification and quality assurance method may include receiving at least one set of first medical images of at least a portion of a patient. A three-dimensional model of the portion of the patient may be created based on the at least one set of first medical images. At least one dosimeter may be inserted into at least a portion of the model. The dosimeter is configured to measure exposure to radiation. The model may be irradiated in accordance with a radiotherapy treatment plan created by a treatment planning system. A readout of the model may be taken or performed to measure in three-dimensions a delivered radiation doses distribution.

18 Claims, 11 Drawing Sheets
(3 of 11 Drawing Sheet(s) Filed in Color)

(56) References Cited

U.S. PATENT DOCUMENTS

| | | |
|---|---|---|
| 2007/0020598 A1 | 1/2007 | Yamashita et al. |
| 2007/0020793 A1 | 1/2007 | Adamovies |
| 2007/0043286 A1 | 2/2007 | Lu et al. |
| 2008/0081991 A1 | 4/2008 | West et al. |
| 2011/0312097 A1 | 12/2011 | Hiroki et al. |
| 2013/0217947 A1 | 8/2013 | Fishman |
| 2016/0166857 A1* | 6/2016 | Nelms .................. A61N 5/1031 600/1 |
| 2016/0279445 A1* | 9/2016 | Ju ........................ A61N 5/1075 |

FOREIGN PATENT DOCUMENTS

| | | |
|---|---|---|
| CN | 101907721 A | 12/2010 |
| JP | 2004348095 | 12/2004 |
| WO | 2007064951 | 6/2007 |
| WO | 2008095068 | 8/2008 |
| WO | 2013076056 | 5/2013 |
| WO | 2014148794 | 9/2014 |

OTHER PUBLICATIONS

Breseman et al., Constructing 3D-Printable CAD models of Prostates from MR Images, 2013 39th Annual Northeast Bioengineering Conference.

Baldock et al., Polymer gel dosimetry, Phys. Med. Biol. 55 (2010) R1-R63.

Sun et al., Using the Full Scale 3D Solid Anthropometric Model in Radiation Oncology Positioning and Verification, 2004, 3432-3435.

Rengier et al., 3D Printing Based on Imaging Data: review of medical applications, Int J CARS (2010) 5:335-341.

\* cited by examiner

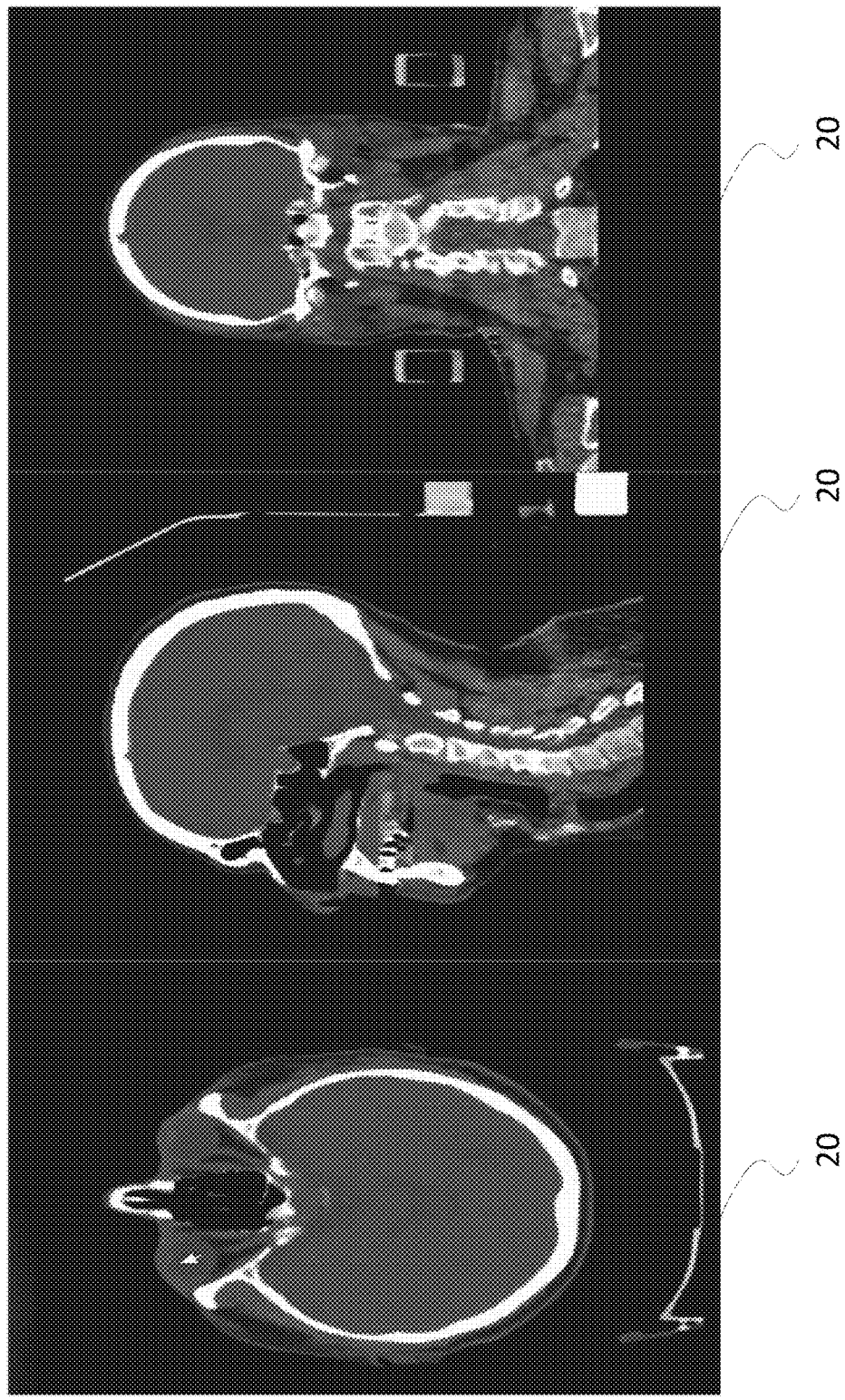

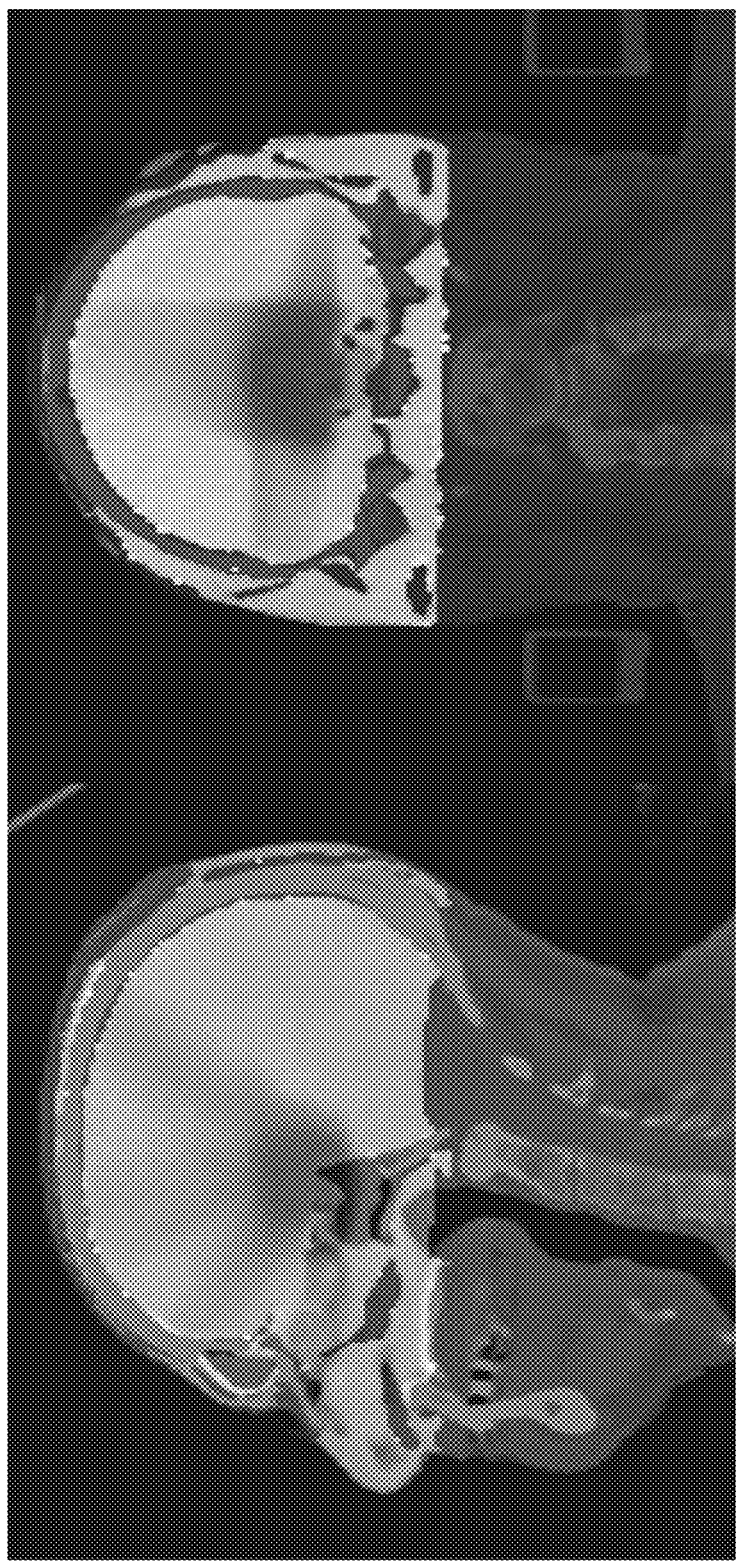

SYSTEM AND METHOD FOR PATIENT-SPECIFIC RADIOTHERAPY TREATMENT VERIFICATION AND QUALITY ASSURANCE SYSTEM

CROSS-REFERENCE TO RELATED APPLICATION

This application is a continuation of PCT/IB14/02624 filed Sep. 9, 2014 which claims priority to U.S. Provisional Application No. 61/876,269, filed Sep. 11, 2013 and entitled "Patient-Specific Radiotherapy Treatment Verification and Quality Assurance Method," the disclosure of which is herein incorporated by reference.

BACKGROUND

Radiation therapy or radiotherapy (RT) is a common curative procedure to treat cancer. The goal of the radiotherapy process is to expose the tumor to a sufficient dose of radiation so as to eradicate all cancer cells. The radiation dose is often close to the tolerance level of the normal body tissues. Therefore, it is necessary to determine the dosage levels in different parts of the irradiated body with high accuracy and precision.

Recent advances in radiological and biological imaging have improved cancer diagnosis and treatment. For radiation therapy, these advances make it possible to accurately delineate a tumor and radioresistant subvolumes inside a tumor. Consequently, complex and heterogeneous dose deliveries are often required. Modern radiotherapy techniques, such as Intensity Modulated Radiotherapy (IMRT), Volumetric Arc Therapy (VMAT), Stereotactic Radiosurgery/Radiotherapy (SRS/SRT), and Proton Therapy (PT), make it possible to implement such complex dose patterns.

As radiation therapy becomes ever more customizable to each individual patient, the complexities of the supporting treatment planning system (TPS) and the dose delivery system increase. This, in turn, necessitates an improvement in quality assurance (QA) methods used to verify the performance of the systems and to implement reliable pretreatment plan verification (PTPV) in clinical practice.

Therefore these complex radiotherapy procedures require sophisticated treatment planning, optimization of the radiation field, and verification of the delivery of the planned dose before the patient is subjected to radiotherapy. It is desirable to have the ability to measure the effects of the planned treatment fields with high accuracy and sensitivity in a three-dimensional volume of clinically relevant dimensions.

SUMMARY

The verification of patient treatment dosages typically is accomplished with dose measurement phantoms. The phantom simulates the body tissue and utilizes dosimeters to measure the radiation dosage before the treatment process on the patient is commenced. Conventional phantoms, however, are not patient specific.

In general, the present disclosure provides, according to certain embodiments, systems and methods for patient-specific radiotherapy treatment plan verification and quality assurance. Such methods and systems generally may comprise receiving at least one set of first medical images of at least a portion of a patient; creating a three-dimensional model of the portion of the patient based on the at least one first medical image; inserting a dosimeter into a portion of the three-dimensional model, the dosimeter being configured to measure exposure to radiation; irradiating at least a portion of the three-dimensional model containing the dosimeter in accordance with a radiotherapy treatment plan; and scanning the irradiated three-dimensional model containing the dosimeter to provide at least one readout image. The step of scanning may be performed by a medical imaging device (e.g., an MRI scanner).

In one exemplary embodiment, the present disclosure is directed to a personalized (patient-specific) treatment plan verification procedure, which increases the accuracy and efficiency of modern radiotherapy techniques. In at least one embodiment, this procedure may be based on high spatial resolution (e.g., ~1×1×1 mm$^3$), full volumetric, three-dimensional ("3D") dosimetry performed with MRI-based polymer gel dosimetry techniques.

One embodiment includes the production by 3D printing technology and use of at least a partially hollow model or phantom designed to duplicate at least a portion of a patient's external anatomy and internal anatomy, at least in terms of bone structures, which is referred to herein as a Patient-Specific Dosimetry Phantom or PSDP. A PSDP may be constructed for each separate patient and may be filled with polymer gel while still in liquid form (such as immediately after gel preparation). The patient-specific treatment planning and irradiation procedure may be applied to the PSDP (i.e., the PSDP may be treated as if it is the real patient). High spatial resolution 3D dose measurements may then be performed by magnetic resonance imaging (MRI) of the irradiated model. These magnetic resonance images, which may include experimentally derived dose data, may be then fused or compared to real patient planning CT images that include the planning target volume (PTV), organs at risk (OAR) and/or the calculated dose pattern. A comparison between the calculated (TPS) and experimentally derived (polymer gel) 3D dose data may then follow and contribute to the completion of the personalized-pretreatment and/or post-treatment plan verification.

The radiation oncologist and/or the medical physicist may be informed or aware before the patient treatment of: (i) the actual 3D-dose pattern to be delivered to the real patient and its differences with the corresponding TPS calculated dose pattern, using the patients anatomy and not a standard geometry of a test dosimetry model (e.g., cube or cylinder that are used currently in clinical practice), and (ii) the accurate geometric position where the dose pattern may or should be delivered relative to the patients external and internal anatomy. Depending on the results (mainly 3D dose comparisons and Dose Volume Histograms (DVH) comparisons (experimental and calculated) and corresponding radiobiological indexes comparisons) new, more appropriate decisions can be made for the irradiation strategy of the real patient. In the same time, a continuous optimization of the TPS and delivery system performance can be implemented (improve geometrical—isocentric accuracy, improve smallphoton-field or proton field dosimetric accuracy and therefore the TPS performance). The present disclosure also contemplates post-treatment, retrospective plan verification using the systems and methods of the present disclosure.

The present disclosure eliminates problems that arise with prior art radiation methods, because the PSDP may duplicate the patient's external contour and internal anatomy in terms of bone structures, allows for the fusion/registration of a reconstructed replica model ("model") and real patient images, and results in personalized treatment verification and patient assurance process.

DRAWINGS

The patent or application file contains at least one drawing executed in color. Copies of this patent or patent application publication with color drawing(s) will be provided by the Office upon request and payment of the necessary fee. The foregoing summary, as well as the following detailed description of the invention, will be better understood when read in conjunction with the appended drawings. For the purpose of illustrating the invention, there are shown in the drawings various illustrative embodiments. It should be understood, however, that the invention is not limited to the precise arrangements and instrumentalities shown.

FIGS. 2A-2C are respectively axial, sagittal, and coronal reconstructions of the CT-scans from FIG. 1.

FIGS. 7A and 7B show a fusion-registration between the image datasets of FIG. 1 and FIG. 5, or FIG. 2A-2C and FIGS. 6A-6C. The background is the real patient CT-scans and the brighter images (that include the dark high dose region) are the irradiated PSDP MR images. The dark area is the experimental dose measured area.

Figure 8B:
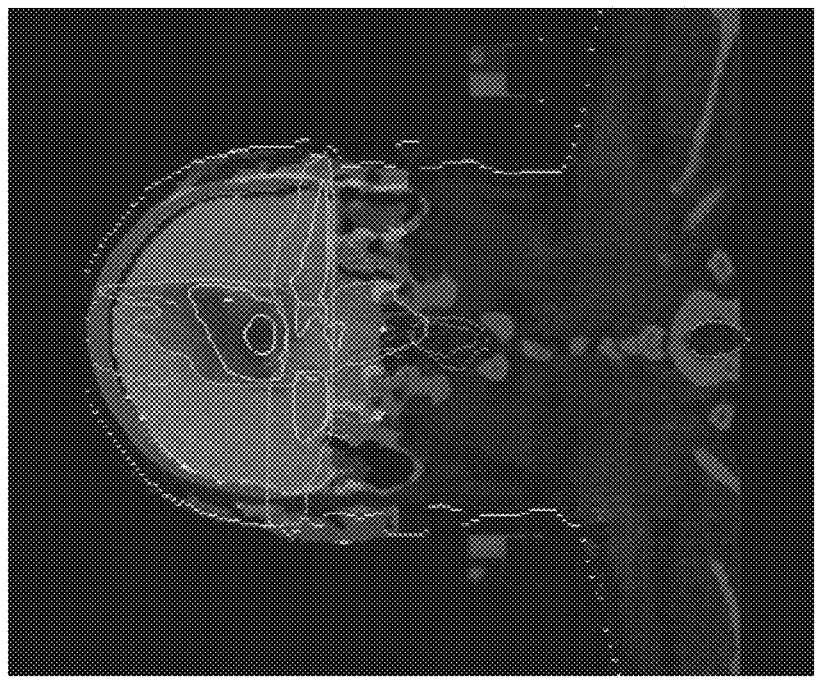
Figure 8A:
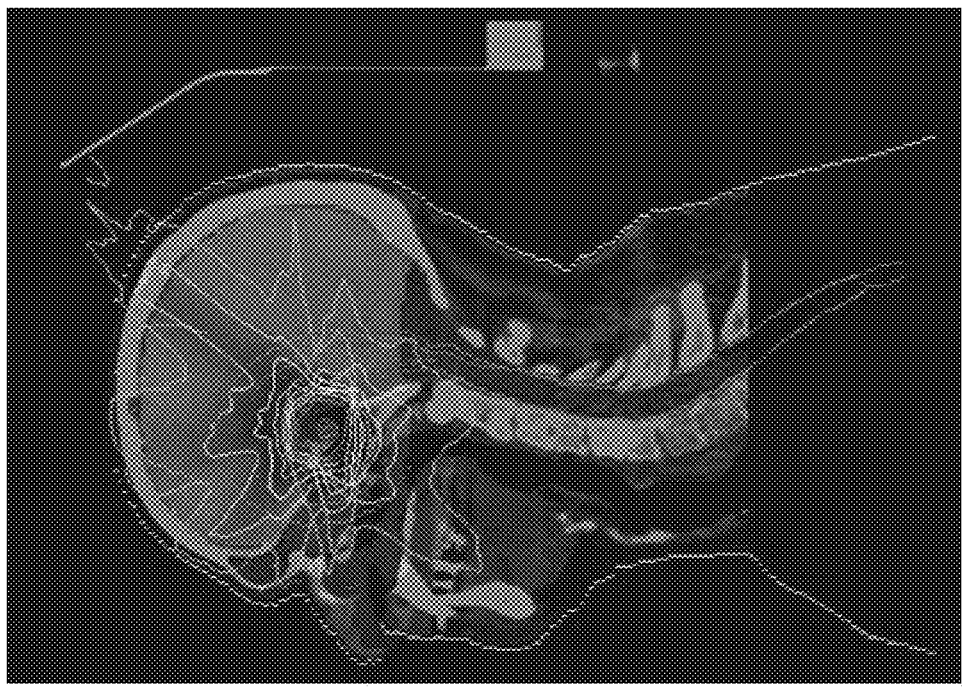

FIGS. 8A and 8B show the fusion-registration of FIGS. 7A and 7B with a TPS theoretical dose calculation superimposed (colored isodose lines).

Figure 9:
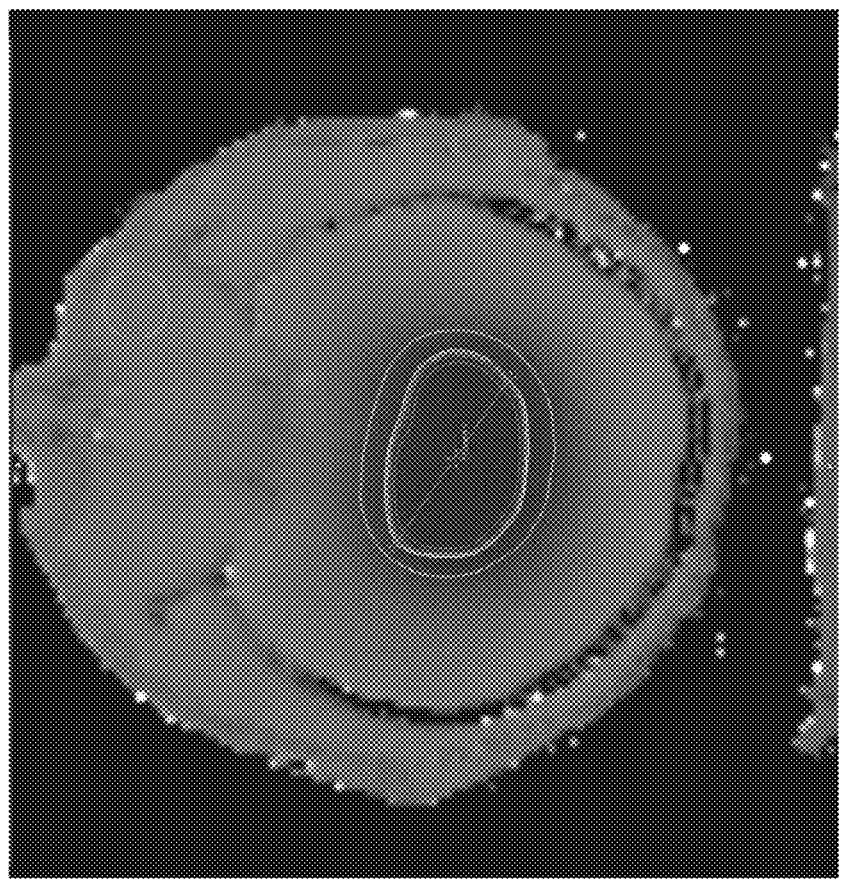
Figure 10:
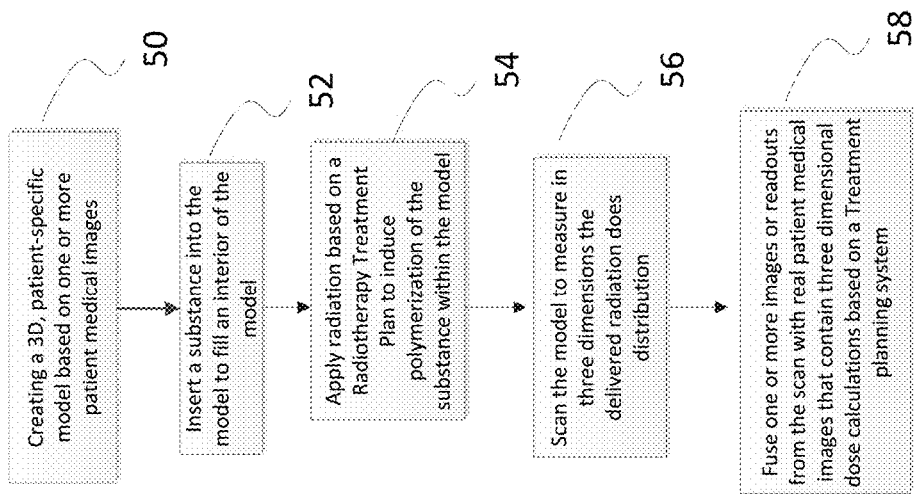

FIG. 9 is a registered-fused image of real patient CT-images and model MM images according to an embodiment of the present disclosure;

FIG. 10 is a flow diagram of a method according to an embodiment of the present disclosure.

Figure 11:
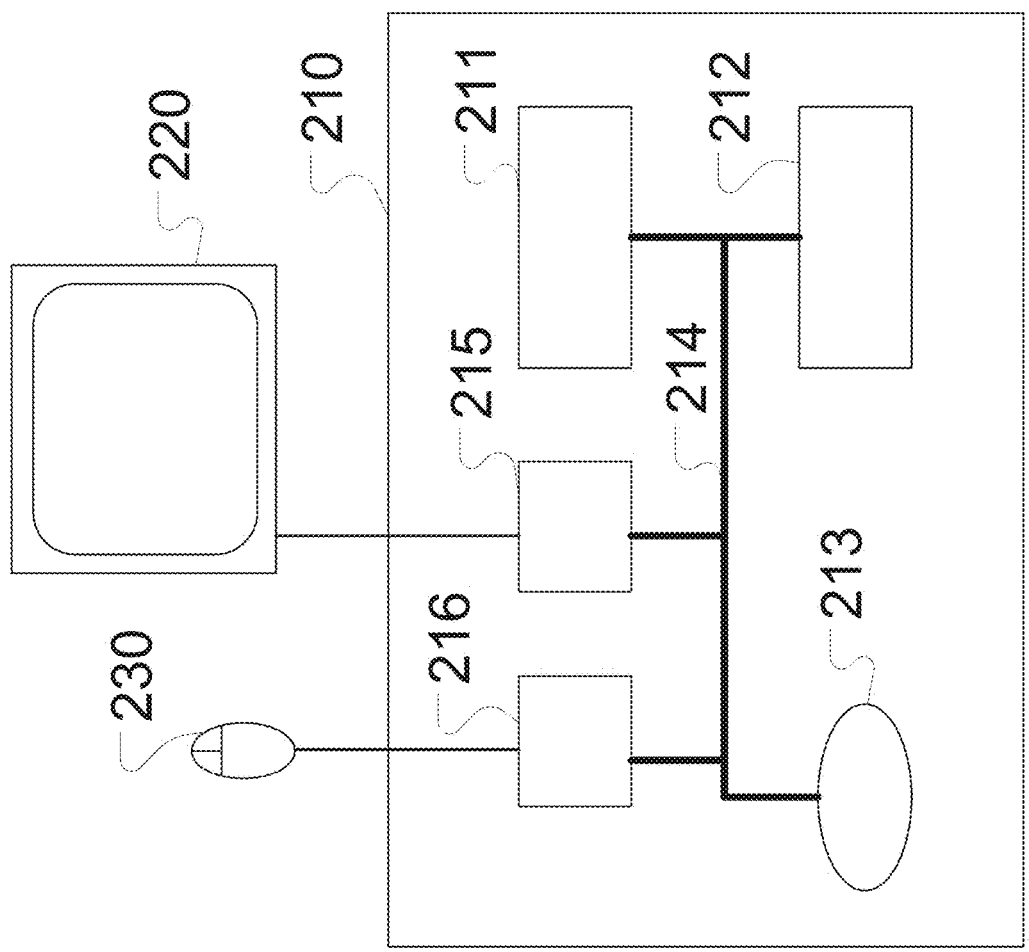

FIG. 11 is a schematic diagram of an exemplary computing device useful for performing at least certain processes disclosed herein.

DETAILED DESCRIPTION

The present disclosure generally relates to patient-specific radiotherapy treatment plan verification and quality assurance systems, devices, and methods. Certain terminology is used in the following description for convenience only and is not limited. Unless specifically set forth herein, the terms "a," "an" and "the" are not limited to one element, but instead should be read as "at least one."

The system or method of the present disclosure may include taking or receiving one or more sets of radiotherapy medical images of at least a portion of a live patient (e.g., cranial region and/or thoracic region). The radiotherapy medical images may include one or more of x-ray computed tomography (CT) images, Magnetic resonance images (MRI), positron emission tomography (PET) images, and the like, or any combination thereof. Such images may be collected in accordance with a treatment planning system (TPS) for determination of the region to be irradiated, as well as the determination of regions that should be protected from radiation.

The set(s) of radiotherapy medical images may be used to create a three-dimensional model of a portion of the patient, which is referred to herein as a Patient-Specific Dosimetry Phantom or PSDP. An example of a PSDP is shown in FIG. 3. The PSDP may include either or both internal bone structures and/or organs, as well as the external surface contours. Stated differently, the PSDP may replicate or duplicate a specific patient anatomy, such as a head or neck or chest, in terms of external contour and bone structure (internal and external). Thus, each PSDP may be unique or specifically designed for each patient. The PSDP may be formed by rapid prototyping using a three-dimensional (3D) printer. 3D printing allows the production of stable objects of almost any shape. In certain embodiments, the medical images are processed using commercially available software (for example, GEOMAGIC) and printed using commercially available 3D printers (for example, 3Dsystems-Project 3510 HDPlus). When complete, the PSDP may be at least partially hollow, and may be formed of one or more materials such as, for example, ceramic material, a polymeric material (e.g., epoxy, plexiglass) or the like. In certain embodiments, the material used to form at least a portion or the entirety of the PSDP is designed to have properties similar to bone in terms of interaction with ionizing radiation (e.g. CT number greater than about 500 or greater than about 700 or greater than or equal to about 1,000 HU). The PSDP also may have a generally solid exterior periphery, and/or may include one or more spaced-apart openings into the hollow interior. Additionally, the PSDP may comprise compartments for surrogates of various anatomical features such as, for example, brain, bone, and ventricles.

A dosimeter is introduced into at least a portion of the PSDP. The dosimeter may be any item or device suitable for inclusion in the PSDP and configured to measure exposure to radiation; such as a dosimeter, may be inserted at least partially or fully into a portion of the PSDP. Suitable dosimeters include those in which certain optical properties within the dosimeter volume change predictably upon interaction with ionizing radiation. These optical properties are sensitive to parameters like the degree of light scattering, absorbance, refractive index, and combinations of these. Moreover, suitable dosimeters include those in which the spin-spin relaxation time within the dosimeter volume change predictably upon interaction with ionizing radiation. Examples of suitable dosimeters include, but are not limited to, any device, apparatus, or substance that is capable of measuring exposure to radiation, such as a polymer gel dosimeter, one or more one-dimensional (1D) point dosimeters, such as an ion chamber, diode, or the like, one or more linear arrays of 1D point dosimeters, one or more two-dimensional (2D) arrays of point dosimeters or 2D dosimeters, such as a gadiographic or radiochromic film, one or more 3D arrays of point dosimeters, and the like. In certain embodiments, the dosimeter is a polymer gel dosimeter designed to have properties similar to soft tissue in terms of interaction with ionizing radiation (e.g., CT number of about 0 HU or less than about 400 or less than about 100 or less than about 30 or less than about 0). The PSDP may be fabricated around the dosimeter, or the dosimeter may be introduced into the model after fabrication.

In certain embodiments, the dosimeter is a polymer gel dosimeter. The polymer gel dosimeter may record and retain spatial dose deposition information in three dimensions. The polymer gel dosimeter may be formed from a radiation sensitive polymer, which, upon irradiation, polymerizes as a function of the absorbed radiation dose. Suitable polymer gel dosimeters include hydrogels in which selected monomers and cross-linkers are dissolved such that water free radicals formed by irradiation induce the polymerization of the monomers, such that monomers are converted to polymers. The amount of polymer produced may be a function of the absorbed dose. A purpose of the gel matrix is to hold the polymer structures in place, preserving spatial information of the absorbed dose. Such polymer gels may be prepared as a liquid and poured into the three-dimensional model of the portion of the patient where they solidify.

Polymer gel dosimeters are commercially available or known in the art and have proven to be suitable for dosimetric purposes because they exhibit a linear dose response over a wide dynamic range. They are currently employed for research and quality assurance purposes via irradiating them with conventional radiation therapy (RT) devices and subsequently transporting to and imaging with MRI devices.

Figure 4B:
FIGS. 4A and 4B are images showing a PSDP arranged for irradiation according to embodiments of the present disclosure.
Figure 4A:

The PSDP containing the dosimeter may be irradiated according to a treatment plan designed for the live patient. The PSDP may be positioned and irradiated as if it was the live patient. (See, e.g., FIG. 4.). Thereafter, the PSDP may be imaged to determine the radiation dose distribution within the PSDP. For example, where the dosimeter is a polymeric gel, the PSDP may be scanned with MRI and rendered into a patient-specific dosimetric phantom. (See, e.g., FIG. 5 and FIG. 6.) Such dosimetric phantoms also may be converted to radiation dose-maps using polymer gel calibration data.

In certain embodiments, the dosimetric phantom may be combined (i.e., a fusion-registration) with the patient's medical images. (See, e.g., FIG. 7.) Such fusion registration is possible because of the PSDP provides accurate, patient-specific anatomical data. In this way the medical image information with 3D does calculations generated by a treatment planning system may be compared to the 3D dose distribution determined from the patient-specific dosimetric phantom. This comparison may be performed using TPS or any other medical imaging software capable of fusion-registration. Such fusion-registration is facilitated by the correspondence of the bone structure and external contours in the medical image and the PSDP. This quality assurance step assists the radiation oncologist and/or the medical physicist, for example, to explore the dosimetric and geometric accuracy of the treatment plan. This comparison may show the 3D-dose distribution calculated by the TPS against the 3D-dose that was actually delivered using the treatment plan, and/or the special-geometric accuracy of the delivered dose. Thus, the system and method of the present disclosure shows if the actually delivered radiation dose has been delivered to the desired geometric/spatial position with the live patient. Corrections or modifications to the radiotherapy treatment may then be considered or performed based on the system or method of the present disclosure.

As is evident from the discussion herein, the method(s) and/or product(s) of the present disclosure are useful not only for pre-treatment plan verification, but also for post-treatment plan verification, i.e. retrospectively. The post-treatment process can be useful for a patient's medical records as it records how the treatment has been delivered. According to the prior art, the medical record of a patient today is only theoretical. According to the present disclosure, however, the medical record of a patient can include what has actually been done to the specific patient. The method(s) and/or product(s) of the present disclosure are useful in providing information about how the treatment was delivered and what tissues were affected.

The digital information required for delivering the treatment (e.g., TPS and Oncology Information System data for each patient) is stored for a long period of time after the treatment. Therefore, the same treatment that has been delivered to a patient can be reproduced using the PSDP. This may be useful, for example, to substantiate whether treatment was the cause of a side-effect, such as loss of vision due to irradiation of the optic nerve. According to prior art methods and systems, this could not be substantiated (even if the TPS showed something different, because TPS is theoretically calculated based on a number of assumptions). The system and method of the present disclosure replicates what has happened using the same patient anatomical data, and the same treatment digital info. As a result, the overall treatment can be reproduced at any time.

The method(s) and/or product(s) of the present disclosure also may be useful for auditing purposes. Audits of RT departments are routinely performed and the product(s) and method(s) of the present disclosure may be used for such purposes. The system and method(s) of the present disclosure may be used to construct a selected PSDP, and the treatment at the PSDP can be delivered. The comparison between experimental and theoretical (TPS) data may be used in the audit.

Referring now to the drawings in detail, wherein like numerals indicate like elements throughout, FIGS. 1-11 show a system and/or method for personalized (patient-specific) Radiotherapy Treatment Verification (RTV) and Quality Assurance (QA), according to certain embodiments of the present disclosure. As noted above, the system and method of the present disclosure can be applied to each separate radiotherapy patient to achieve a more accurate and effective radiotherapy treatment, and can be used for all radiotherapy modalities and all kinds of ionizing radiations used for performing radiotherapy.

Figure 1:
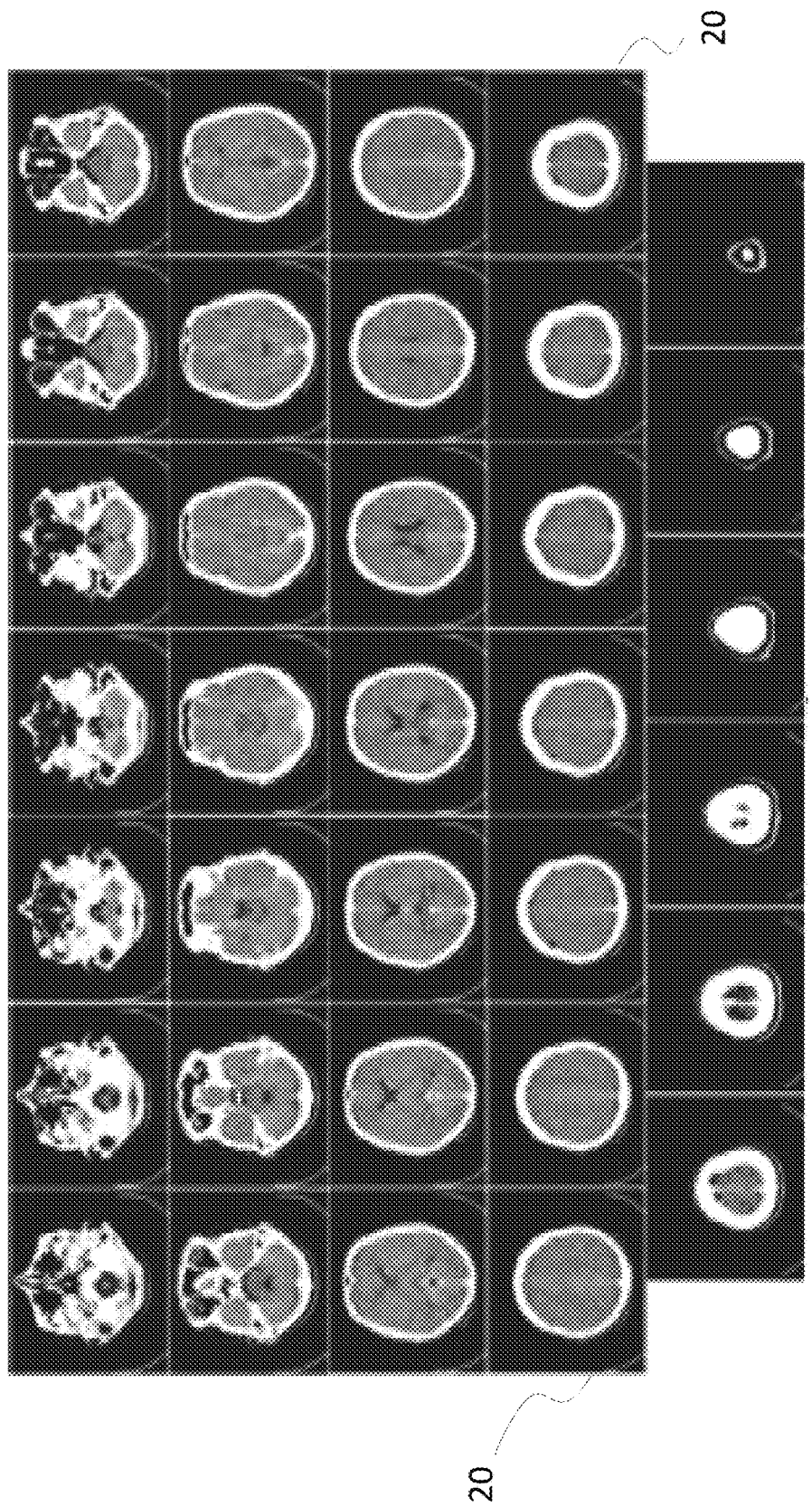
FIG. 1 is a set or collection of medical images from a CT-scan of a patient's actual head.

Referring to FIGS. 1-2C, the system or method of the present disclosure may include taking or receiving one or more sets of radiotherapy medical images 20 of at least a portion of a patient. The present disclosure discusses and shows that the portion of the patent is the skull or head. However, the system or method disclosed herein can be used to more effectively treat any of one or more body parts of a patient, such as the abdominal region. The radiotherapy medical images 20 may include one or more of x-ray computed tomography (CT) images (FIGS. 1, 2A-2C), Magnetic resonance images (MM), positron emission tomography (PET) images, and the like.

Figure 3B:
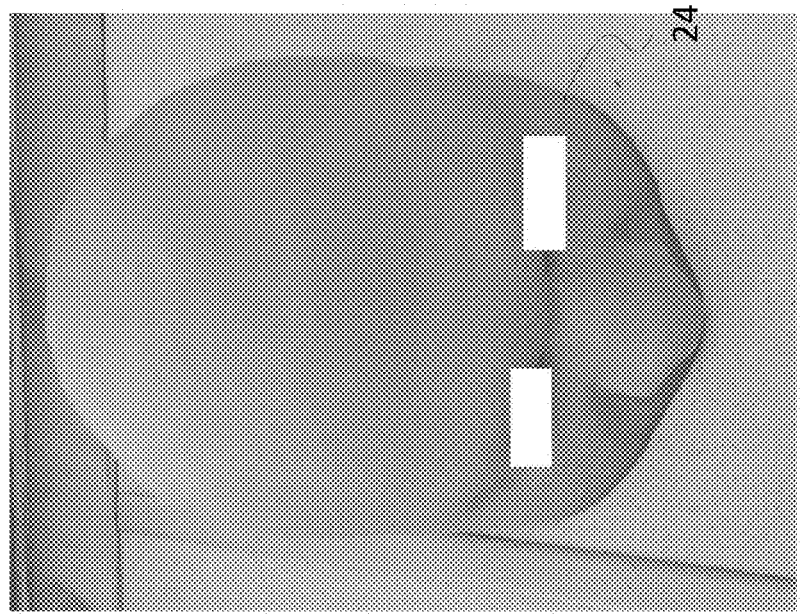
FIGS. 3A and 3B are top perspective views of a PSDP according to embodiments of the present disclosure.
Figure 3A:
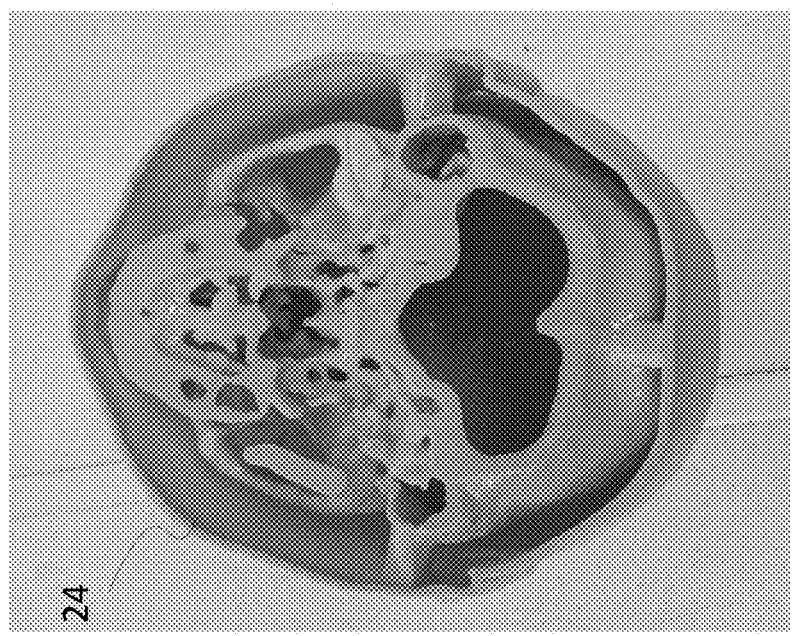

Referring to FIGS. 3A and 3B, in one exemplary embodiment, one or more CT scans 20 may be sent to, or inputted into a three-dimensional (3D) printer. The printer may be configured to print or form one or more PSDPs designed to replicate the one or more portions of the patient shown in the CT scan(s) (step 50 shown in FIG. 10). Thus, each PSDP 24 may be unique or specifically designed for each patient. When complete, each PSDP 24 may be at least partially hollow, and may replicate or duplicate a specific patient's anatomy, such as a skull or neck, in terms of external contour and bone structure (internal and external). The PSDP 24 may have a generally solid exterior periphery (FIG. 3B), and/or may include one or more spaced-apart openings into the at least partially hollow interior. The model 24 is configured to accept or include a dosimeter capable of measuring exposure to radiation. For example, a polymer gel dosimeter in liquid form may be inserted into the PSDP 24 to generally fill the internal, hollow cavity of the PSDP 24 (see step 52 of FIG. 10).

In one exemplary embodiment, the PSDP 24 may be irradiated according to the Radiotherapy Treatment Plan (RTP) created by a Treatment Planning System (TPS) (see step 54 of FIG. 10). As known by those skilled in the art, the RTP is typically used for performing radiotherapy irradiation on a real, live patient. In at least one embodiment of the present application, prior to performing the RTP on the real, live patient, the RTP may be performed "tested" on the PSDP 24 for personalized radiotherapy treatment verification and quality assurance. For example, where the PSDP 24 is of the patient's head, the PSDP 24 may be positioned in the treatment room and irradiated exactly as if the PSDP 24 were the real patient (see FIGS. 4A and 4B)

Figure 5:
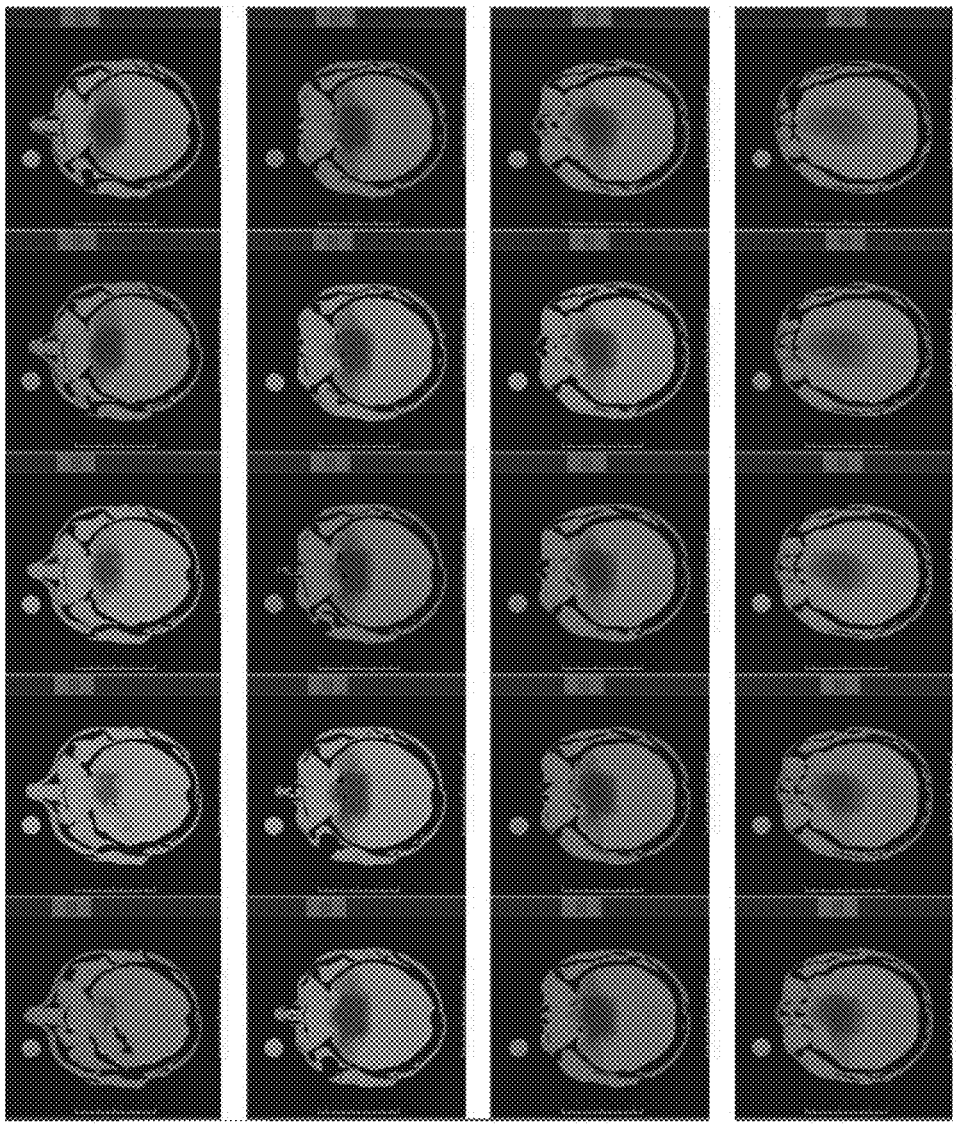
FIG. 5 is a set or collection of readout images (a spin-spin relaxation time (T2) map (axial slice)) from an MRI scan of an irradiated PSPD according to embodiments of the present disclosure.
Figures 6A, 6B, 6C:
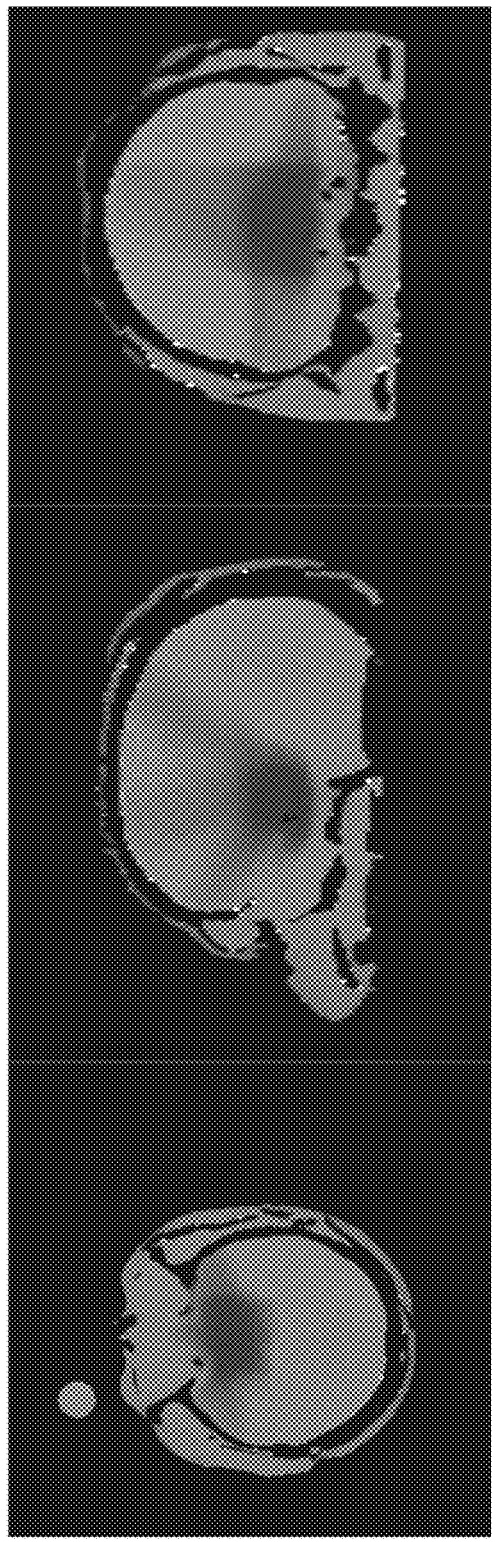
FIGS. 6A-6C are respectively axial, sagittal, and coronal images of the PSDP reconstructed from the images presented in FIG. 5.

Referring to FIGS. 5 and 6, in one exemplary embodiment, the PSDP 24 is scanned using MRI, for example, in order to measure in three dimensions the delivered dose distribution (see step 56 of FIG. 10) within the PSDP 24. A 3D-MRI scan of all of the irradiated volume of the PSDP 24 may result in high spatial resolution 3D-T2-parametric maps or standard clinical T2 weighted images. The darker areas in FIG. 5 and FIG. 6 readout images represent a high-dose area. In operation, the lower the T2-value, as assessed by T2 maps, the higher the dose. By using polymer gel calibration data [D=f(T2), D: dose], the parametric T2-maps can be converted to actual radiation dose-maps.

FIGS. 7A and 7B show a fusion registration or comparison between the real patient CT-images and the PSDP 24 MM images (see step 58 of FIG. 10). The CT-images may contain the TPS calculated dose distributions, and the MRI images may contain the polymer gel measured dose distributions. Accordingly, the TPS theoretical dose calculations (colored isodose lines) may be superimposed with the fusion registration, as shown in FIGS. 8 and 9. This allows qualitative and/or quantitate comparisons and evaluation of the overall treatment. For example, where the dose pattern reveals a problem (e.g., that the dose pattern will affect a critical organ), the treatment plan can be modified.

One or more of the above-described techniques and/or embodiments may be implemented with or involve software, for example modules executed on or more computing devices 210 (see FIG. 10). Of course, modules described herein illustrate various functionalities and do not limit the structure or functionality of any embodiments. Rather, the functionality of various modules may be divided differently and performed by more or fewer modules according to various design considerations.

Each computing device 210 may include one or more processing devices 211 designed to process instructions, for example computer readable instructions (i.e., code), stored in a non-transient manner on one or more storage devices 213. By processing instructions, the processing device(s) 211 may perform one or more of the steps and/or functions disclosed herein. Each processing device may be real or virtual. In a multi-processing system, multiple processing units may execute computer-executable instructions to increase processing power. The storage device(s) 213 may be any type of non-transitory storage device (e.g., an optical storage device, a magnetic storage device, a solid state storage device, etc. The storage device(s) 213 may be removable or non-removable, and may include magnetic disks, magneto-optical disks, magnetic tapes or cassettes, CD-ROMs, CD-RWs, DVDs, BDs, SSDs, or any other medium which can be used to store information. Alternatively, instructions may be stored in one or more remote storage devices, for example storage devices accessed over a network or the internet.

Each computing device 210 additionally may have memory 212, one or more input controllers 216, one or more output controllers 215, and/or one or more communication connections 240. The memory 212 may be volatile memory (e.g., registers, cache, RAM, etc.), non-volatile memory (e.g., ROM, EEPROM, flash memory, etc.), or some combination thereof. In at least one embodiment, the memory 212 may store software implementing described techniques.

An interconnection mechanism 214, such as a bus, controller or network, may operatively couple components of the computing device 210, including the processor(s) 211, the memory 212, the storage device(s) 213, the input controller(s) 216, the output controller(s) 215, the communication connection(s) 240, and any other devices (e.g., network controllers, sound controllers, etc.). The output controller(s) 215 may be operatively coupled (e.g., via a wired or wireless connection) to one or more output devices 220 (e.g., a monitor, a television, a mobile device screen, a touch-display, a printer, a speaker, etc.) in such a fashion that the output controller(s) 215 can transform the display on the display device 220 (e.g., in response to modules executed). The input controller(s) 216 may be operatively coupled (e.g., via a wired or wireless connection) to an input device 230 (e.g., a mouse, a keyboard, a touch-pad, a scroll-ball, a touch-display, a pen, a game controller, a voice input device, a scanning device, a digital camera, etc.) in such a fashion that input can be received from a user.

The communication connection(s) 240 may enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

FIG. 11 illustrates the computing device 210, the output device 220, and the input device 230 as separate devices for ease of identification only. However, the computing device 210, the display device(s) 220, and/or the input device(s) 230 may be separate devices (e.g., a personal computer connected by wires to a monitor and mouse), may be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). The computing device 210 may be one or more servers, for example a farm of networked servers, a clustered server environment, or a cloud services running on remote computing devices.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:
1. A method comprising:
    receiving medical images of one patient;
    creating a patient-specific three-dimensional model of a portion of the one patient based only on the medical images of the one patient;
    inserting a dosimeter into the patient-specific three-dimensional model, the dosimeter being configured to measure exposure to radiation;
    scanning the patient-specific three-dimensional model containing the dosimeter to provide at least one control readout image representing the patient-specific three-dimensional model;

irradiating at least a portion of the patient-specific three-dimensional model containing the dosimeter according to a patient-specific radiotherapy treatment plan to yield an irradiated patient-specific three-dimensional model; and scanning the irradiated patient-specific three-dimensional model to provide at least one irradiated readout image representing a radiation dose distribution within the irradiated patient-specific three-dimensional model, wherein the at least one irradiated readout image is a three-dimensional image.

2. The method of claim 1, further comprising fusion-registration of (a) the at least one irradiated readout image with, (b) the at least one control readout image.

3. The method of claim 1, further comprising fusion-registration of (a) the at least one irradiated readout image with, (b) the at least one control readout image with, (c) at least one three-dimensional dose distribution calculated by the patient-specific radiotherapy treatment plan.

4. The method of claim 1, further comprising fusion-registration of (a) the at least one irradiated readout image with, (b) the at least one control readout image with, (c) at least one three-dimensional dose distribution calculated by the patient-specific radiotherapy treatment plan with, (d) the medical images of the one patient.

5. The method according to claim 1, wherein the dosimeter is a polymer gel dosimeter.

6. The method according to claim 1, wherein the dosimeter is at least one of a point dosimeter, a linear array of point dosimeters, a two-dimensional array of point dosimeters, a three-dimensional array of point dosimeters, and at least one two-dimensional dosimeter.

7. The method according to claim 1, wherein the medical images are taken by at least one of computed tomography, magnetic resonance imaging, and positron emission tomography.

8. The method according to claim 1, wherein the step of creating the patient-specific three-dimensional model is performed by three-dimensional printing.

9. The method according to claim 1, wherein the patient-specific three-dimensional model is at least partially hollow.

10. The method according to claim 1, wherein the dosimeter is inserted into a hollow cavity of the patient-specific three-dimensional model.

11. The method according to claim 1, wherein the step of scanning the irradiated patient-specific three-dimensional model comprises magnetic resonance imaging.

12. A method comprising:
receiving medical images of one patient;
creating a patient-specific three-dimensional model of a portion of the one patient based only on the medical images of the one patient;
inserting a dosimeter into the patient-specific three-dimensional model, the dosimeter being configured to measure exposure to radiation;
irradiating at least a portion of the patient-specific three-dimensional model containing the dosimeter according to a patient-specific radiotherapy treatment plan to yield an irradiated patient-specific three-dimensional model; and
scanning the irradiated patient-specific three-dimensional model to provide at least one irradiated readout image representing a radiation dose distribution within the irradiated patient-specific three-dimensional model, wherein the at least one irradiated readout image is a three-dimensional image.

13. The method of claim 12, further comprising fusion-registration of (a) the at least one irradiated readout image with, (b) the medical images of the one patient.

14. The method of claim 12, further comprising fusion-registration of (a) the at least one irradiated readout image with, (b) the medical images of the one patient with, (c) at least one three-dimensional dose distribution calculated by the patient-specific radiotherapy treatment plan.

15. The method according to claim 12, wherein the dosimeter is a polymer gel dosimeter.

16. The method according to claim 12, wherein the dosimeter is at least one of a point dosimeter, a linear array of point dosimeters, a two-dimensional array of point dosimeters, a three-dimensional array of point dosimeters, and at least one two-dimensional dosimeter.

17. The method according to claim 12, wherein the at least one set of first medical images is taken by at least one of computed tomography, magnetic resonance imaging, and positron emission tomography.

18. The method according to claim 12, wherein the step of scanning the irradiated patient-specific three-dimensional model comprises magnetic resonance imaging.

* * * * *